United States Patent
Burns et al.

(10) Patent No.: US 10,143,447 B2
(45) Date of Patent: Dec. 4, 2018

(54) SKIN SURFACE SAMPLING SYSTEM

(71) Applicant: Conopco,Inc., Englewood Cliffs, NJ (US)

(72) Inventors: Corrinne Burns, London (GB); Peter David Carroll, Hoylake (GB); Pareenkumar Patel, Loughborough (GB); Svetlana Riazanskaia, Meols (GB); Charles Lawrence Paul Thomas, Loughborough (GB)

(73) Assignee: Conopco, Inc., Englewood Cliffs, NJ (US)

( * ) Notice: Subject to any disclaimer, the term of this patent is extended or adjusted under 35 U.S.C. 154(b) by 986 days.

(21) Appl. No.: 14/399,629

(22) PCT Filed: Apr. 15, 2013

(86) PCT No.: PCT/EP2013/057768
§ 371 (c)(1),
(2) Date: Nov. 7, 2014

(87) PCT Pub. No.: WO2013/167349
PCT Pub. Date: Nov. 14, 2013

(65) Prior Publication Data
US 2015/0119755 A1  Apr. 30, 2015

(30) Foreign Application Priority Data
May 10, 2012 (EP) ..................... 12167428

(51) Int. Cl.
*A61B 10/00* (2006.01)
*G01N 1/14* (2006.01)
(Continued)

(52) U.S. Cl.
CPC .......... *A61B 10/0064* (2013.01); *A61B 10/00* (2013.01); *G01N 1/14* (2013.01);
(Continued)

(58) Field of Classification Search
CPC ...... A61B 10/0064; A61B 10/00; G01N 1/24; G01N 1/14; G01N 2001/383; G01N 2001/028
See application file for complete search history.

(56) References Cited

U.S. PATENT DOCUMENTS

| 2002/0045912 A1 | 4/2002 | Ignotz |
| 2004/0147885 A1 | 7/2004 | Tsuda et al. |

(Continued)

FOREIGN PATENT DOCUMENTS

| EP | 2109762 | 9/2011 |
| EP | 2420190 | 2/2012 |

OTHER PUBLICATIONS

Search Report in EP12167428, dated Sep. 12, 2012.
(Continued)

*Primary Examiner* — Sean Dougherty
(74) *Attorney, Agent, or Firm* — Greenberg Traurig, LLP

(57) ABSTRACT

The present invention provides a skin surface sampling device in which a supply tube and a recovery tube are housed in an elongated hand-holdable tubular sleeve, the sleeve having upper and lower ends positioned along a longitudinal axis and the lower end being provided with a sampling head; in which: the supply tube is adapted to convey liquid from a liquid source to the sampling head; the recovery tube is adapted to convey liquid from the sampling head to a liquid collection vessel; the sampling head has a planar surface adapted for application to the surface of the skin to form a contact therewith during sampling; the planar surface has a liquid entry port adapted for liquid communication with the supply tube and a liquid exit port adapted for liquid communication with the recovery tube; and characterized in that: the liquid entry port and the liquid exit port are connected via a guide channel which is adapted to guide liquid from the liquid entry port, along the surface of the skin
(Continued)

for the elution of materials on the skin surface, and then to the liquid exit port for recovery. The device can be used in a rapid and non-invasive system of skin surface sampling, enabling the sampling of a wide range of compounds (including but not limited to VOCs and SVOCs) from the surface of the skin, and which can be used over all areas of the body.

6 Claims, 2 Drawing Sheets

(51) Int. Cl.
*G01N 1/24* (2006.01)
*G01N 1/02* (2006.01)
*G01N 1/38* (2006.01)

(52) U.S. Cl.
CPC ......... *G01N 1/24* (2013.01); *G01N 2001/028* (2013.01); *G01N 2001/383* (2013.01)

(56) References Cited

U.S. PATENT DOCUMENTS

2008/0190218 A1* 8/2008 Riazanskaia ............. G01N 1/22
73/864
2011/0283776 A1 11/2011 Wu

OTHER PUBLICATIONS

Search Report in PCTEP2013057768, dated Jun. 25, 2014.
Written Opinion in EP12167428, dated Sep. 12, 2012.
Written Opinion in PCTEP2013057768, dated Apr. 15, 2013.

\* cited by examiner

SKIN SURFACE SAMPLING SYSTEM

FIELD OF THE INVENTION

The present invention relates to skin surface sampling.

BACKGROUND OF THE INVENTION AND PRIOR ART

Volatile organic compounds (VOC) and semi-volatile organic compounds (SVOC) present on the skin are derived from four processes: glandular secretions from the eccrine, apocrine and sebaceous glands within the skin; exogenous inputs to the skin (such as environmental contamination, topically applied medications as well as personal care and cosmetic formulations); perfusion of compounds from the underlying blood vessels; and the products and by-products of micro-biological metabolism.

Accordingly, the skin profile of VOCs and SVOCs is rich and dynamic and dependent on factors such as the body's metabolic or hormonal state, ingested dietary compounds, variations in the external environment (such as diurnal and seasonal), the particular body site which is sampled, and the bacterial species colonizing the skin surface.

It is becoming increasingly apparent that the information contained in an individual's skin profile of VOCs and SVOCs is a resource of great potential from an analytical perspective. For example, human volatile chemical profiles show promise as a means of diagnosis and health monitoring. Also in non-clinical areas such as cosmetics, toiletries and personal care, understanding of the chemicals related to skin odour could lead to development of more effective deodorant, antiperspirant or fragrance products.

Current skin surface sampling methods are generally focussed on collecting sweat as it exudes from the participant's skin. Such methods are often unsatisfactory since there is little control over the region from which the sweat will be derived. Also thermal stress or intense exercise is usually required in such methods to induce sweating. Therefore the samples are not representative of the range of sweating mechanisms that exist, and the findings cannot necessarily be applied to subjects who might be frail, very young or elderly.

EP 2 109 762 describes an alternative approach in which VOCs are trapped directly from the skin, using a sampler employing a hydrodynamic gas flow to volatilise substances from the skin surface and convey the substances to a collector. The sampler has a gas supply coupled to a hand-held probe that comprises a supply tube, a recovery tube and a skirt. The gas is expelled under pressure through one of the tubes onto the skin surface and recovered through the second tube to the collector. Although this technique eliminates many of the problems involved in sweat sampling, its applicability is limited to the recovery of those substances which are volatile enough to be entrained in the flow of gas.

The object of the present invention is to provide a rapid and non-invasive system of skin surface sampling, which can be used to sample a wide range of compounds (including but not limited to VOCs and SVOCs) from the surface of the skin, and which can be used over all areas of the body. Advantageously, analysis of the samples collected using the system of the invention shows that different body parts may be consistently distinguished, thus allowing rapid, non-invasive chemical mapping of the human body.

SUMMARY OF THE INVENTION

The present invention provides a skin surface sampling device in which a supply tube and a recovery tube are housed in an elongated hand-holdable tubular sleeve, the sleeve having upper and lower ends positioned along a longitudinal axis and the lower end being provided with a sampling head;
in which:
the supply tube is adapted to convey liquid from a liquid source to the sampling head;
the recovery tube is adapted to convey liquid from the sampling head to a liquid collection vessel;
the sampling head has a planar surface adapted for application to the surface of the skin to form a contact therewith during sampling;
the planar surface has a liquid entry port adapted for liquid communication with the supply tube and a liquid exit port adapted for liquid communication with the recovery tube; and characterised in that:
the liquid entry port and the liquid exit port are connected via a guide channel which is adapted to guide liquid from the liquid entry port, along the surface of the skin for the elution of materials on the skin surface, and then to the liquid exit port for recovery.

The sampling head, and in particular the guide channel, are typically designed to facilitate the washing of liquid over the skin surface and to ensure that it does not collect excessively in a static area, rather than travelling across the skin. Desirably a seal is created when the sampling head is lightly pressed onto the skin surface, so that liquid leakage is minimised. Preferably the guide channel has a smooth and/or continuous shape, such as curved, coiled, swirled or serpentine. A particularly preferred shape of guide channel in the context of this invention is a swirl with dimensions approximately 1 mm wide×1 mm deep×35 mm in length.

The invention also provides a skin surface sampling system comprising:
a liquid source;
a liquid collection vessel, and
a skin surface sampling device as defined above.

Preferably, a gentle positive pressure is used to propel liquid out from the liquid source, through the skin surface sampling device, and back to the liquid collection vessel. For example, a positive displacement pump (such as a syringe pump or peristaltic pump) may be fitted to the liquid source.

BRIEF DESCRIPTION OF THE DRAWINGS

The invention will now be described in greater detail, by way of example, with reference to the following drawings. In the drawings.

DETAILED DESCRIPTION OF THE INVENTION

Figure 1:
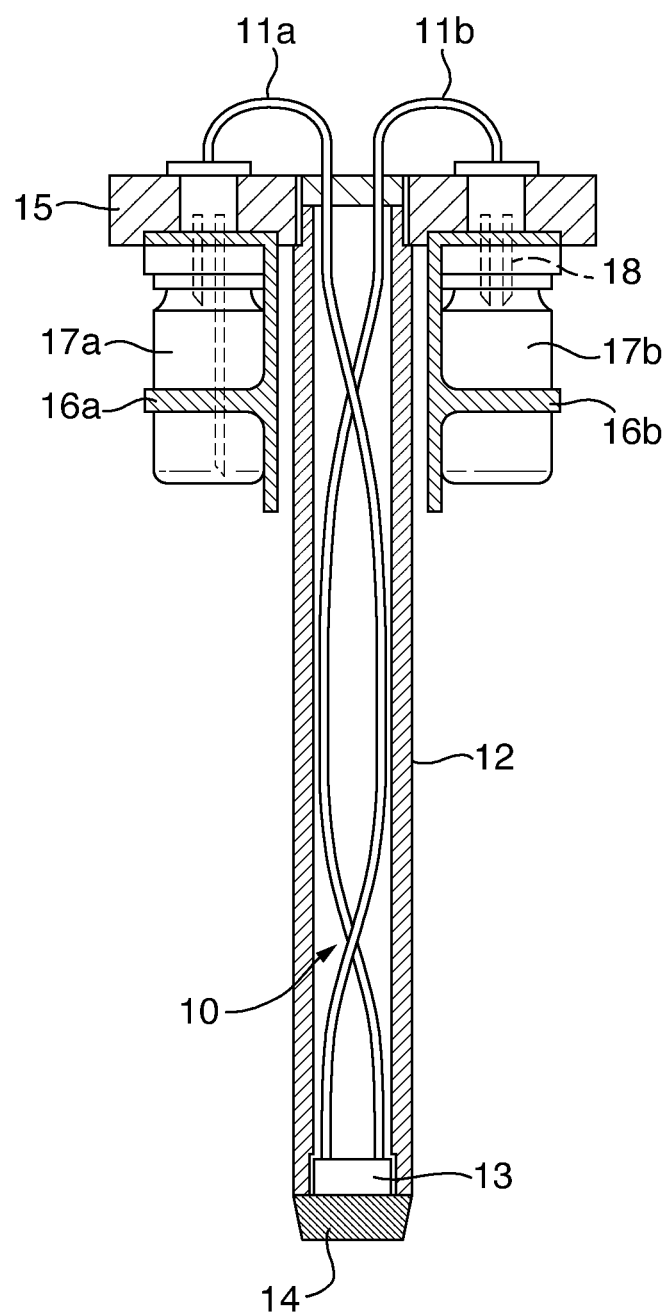
FIG. 1 shows a skin surface sampling system according to the invention in schematic longitudinal section view.

Referring to FIG. 1, a skin surface sampling system of the invention comprises a skin surface sampling device 10 in which supply tube 11a and recovery tube 11b are housed in an elongated hand-holdable tubular outer sleeve 12 made from acrylic. Supply tube 11a and recovery tube 11b are each made from Peek® and measure 1.6 mm diameter×1 mm bore×190 mm length. The open end of sleeve 12 has an internal "O" ring fitted and slides over sampling head bush 13 made from polyetheretherketone (Ketron® Peek® GF30). Attached with a screw thread to sampling head bush 13 is a removable sampling head 14 also made from Peek® GF30.

The skin surface sampling system is set up as follows:

Sleeve 12 is screwed into bottle holder 15 which is provided with retaining clips 16a, 16b for easy loading and unloading of sampling bottles.

Liquid source bottle 17a (containing the desired sampling liquid) and liquid collection bottle 17b (for recovery of the sampling liquid) are loaded into bottle holder 15.

One end of supply tube 11a is pushed through a rubber septum provided at the neck of source bottle 17a. This end of supply tube 11a should make contact with the bottom of bottle 17a, to ensure the bottle will be emptied during the sampling process. The other end of supply tube 11a is connected to sampling head bush 13 by pushing it into a corresponding hole.

One end of recovery tube 11b is pushed through a rubber septum provided at the neck of collection bottle 17b. This end of recovery tube 11b should protrude through the bottle septum by approximately 6 mm, so that sampling liquid can flow freely during the sampling process. The other end of recovery tube 11b is connected to sampling head bush 13 by pushing it into a corresponding hole.

A venting tube 18 is pushed through the rubber septum provided at the neck of collection bottle 17b. This should protrude through the bottle septum by approximately 6 mm, and acts to stop any build up of pressure within the collection bottle 17b.

The outlet of a syringe pump (not shown) is pushed through the rubber septum provided at the neck of liquid source bottle 13a. This should protrude through the bottle septum by approximately 6 mm.

Figure 2:
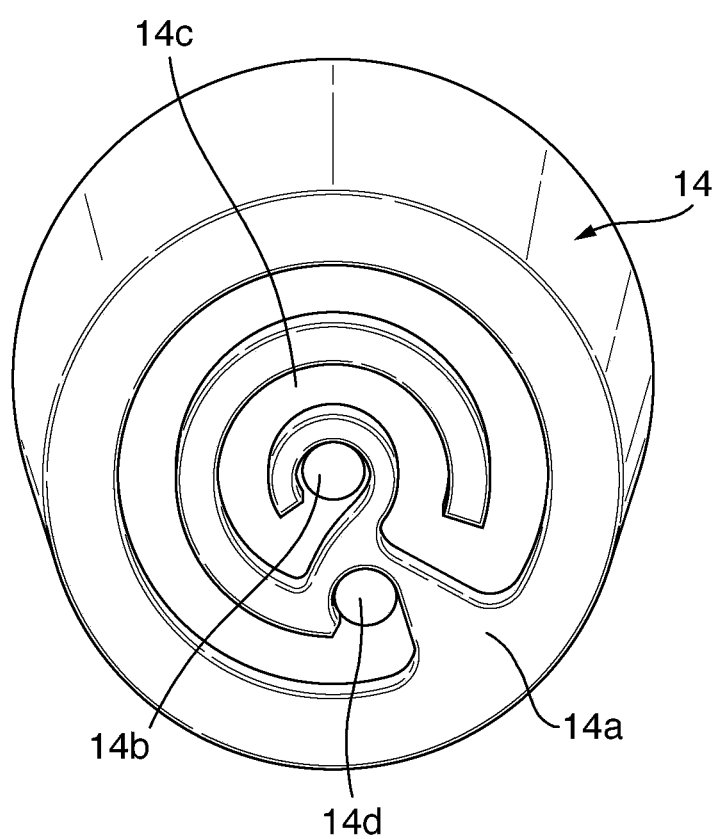
FIG. 2 is a photographic end-on view of the planar surface of the sampling head of a skin surface sampling device according to the invention.

During a typical operation of the skin surface sampling system, the operator holds sleeve 12 of skin surface sampling device 10, and places sampling head 14 in gentle contact with the surface of the skin which is to be sampled. A positive pressure (delivered from the syringe pump) pushes sampling liquid out of liquid source bottle 13a and through supply tube 11a to sampling head 14. Referring to FIG. 2, sampling head 14 has a planar surface 14a which contacts the surface of the skin during sampling. Sampling liquid flowing from supply tube 11a arrives at entry port 14b provided on surface 14a. From entry port 14b the sampling liquid enters swirl-shaped guide channel 14c. The sampling liquid flows through guide channel 14c. During its passage it washes the skin surface and elutes materials therefrom, until it reaches exit port 14d provided at the end of guide channel 14c. From exit port 14d, the sampling liquid is directed back out of the sampling head 14 and through recovery tube 11b, which delivers it into liquid collection bottle 17b. The eluted materials may then be analysed.

The sampling system of the invention may optionally incorporate a vibration motor to encourage the surface washing action of the sampling liquid. In a typical embodiment of such a system, the vibration motor is encapsulated in a stainless steel motor holder connected to a stainless steel tube which is screwed into bottle holder 15. The motor holder is attached using grub screws to sampling head bush 13. Suitable motors are designed to run at 11,000 rpm for up to one minute, the approximate time it takes to empty one bottle during the sampling process. Suitably, the vibration motor is powered by using one 1.5V battery mounted inside a battery holder with an on/off button attached. Cables from the vibration motor run inside the stainless steel tube and connect to the on/off switch. A mains power supply could also be used if prolonged use of the system is required.

Example 1

In this Example, a skin surface sampling system as described above was used to sample the surface of the skin at various different sites on the human body.

Sampling Procedure

Test participants refrained from using perfumed soap, shampoo and deodorant for three weeks prior to the start of skin sampling. Participants were provided with unperfumed cosmetics, were allowed to use these as frequently as necessary. Participants were asked not to wash in the twenty-four hours preceding skin sampling, and were given new cotton T-shirts to wear during this time.

In the sampling procedure, Two 2 ml glass vials, each with 1 mm screw neck and 11 mm cap with rubber septum, were connected to the sampling device as described above. The source vial contained 1 ml of a 1:1 mixture of benzene-free ethanol and double distilled water. The collection vial was empty. Vials were pushed through the needles of the sampling device, and fitted into place.

The sampling device was connected to a peristaltic pump (Watson Marlow 120U with Bioprene tubing of 1.6 mm wall and 1.6 mm bore size), via an inlet in the top of the device, above the collection vial.

Sampling sites were washed with double deionised water and dried with cotton wool. Then, the peristaltic pump was set to 32 rpm, and the head of the sampling device placed so that it was in gentle contact with the skin surface. The device directed a constant flow of ethanol and water across the skin surface. This sampling process lasted about two minutes, by which time all of the ethanol: water mixture had crossed the skin's surface, and passed into the collection vial.

The device was used to collect forty samples from the surface of human skin: underarm, anterior elbow, upper foot and lower foot.

Sample collection was rapid, averaging at 1 minute collection time per body part. Participants did not report any discomfort during the sampling process.

Analytical Procedure

Samples were refrigerated until analysis, the same day, by direct injection electrospray mass spectrometry (MS-ESI) on a Waters Liquid Chromatography Time Of Flight (TOF) mass spectrometer in positive ion mode. The desorption temperature, in the spray chamber, was held at 300° C., with a gas flow of 350 L/h. The sample cone gas flow was 24 L/h. The source temperature was 100° C. The capillary voltage was 3500 V. The sample cone was set to 30 V, and the extraction cone at 5 V. RF lens was set to 200. Samples were infused to the spray chamber at 300·l/hour, and visualised using MassLynx software. The MS was calibrated for mass accuracy prior to analysis. Blank instrument samples and solvent samples were analysed alongside human skin samples. Samples were analysed in negative ion mode on a Synapt Electrospray MS.

Statistical Processing

Principal Components Analysis (PCA) was performed using SIMCA P+ version 12.

Results

Upon electrospray-MS analysis, clear differences in SVOC profile could be observed between body parts in all participants. Underarm showed the richest profile, followed by lower foot, upper foot, and anterior elbow. m/z values unique to each of these body parts were consistently obtained.

The invention claimed is:

1. A skin surface sampling device comprising a supply tube and a recovery tube housed in an elongated hand-holdable tubular sleeve, the sleeve having upper and lower ends positioned along a longitudinal axis and the lower end being provided with a sampling head;

wherein:
- the supply tube is adapted to convey liquid from a liquid source to the sampling head;
- the recovery tube is adapted to convey liquid from the sampling head to a liquid collection vessel;
- the sampling head has a planar surface adapted for application to the surface of skin to form a seal by contact therewith during sampling;
  - wherein the planar surface is in contact with the surface of the skin during sampling;
- the planar surface has a liquid entry port adapted for liquid communication with the supply tube and a liquid exit port adapted for liquid communication with the recovery tube;

and characterised in that:
- the liquid entry port and the liquid exit port are connected via a guide channel which is adapted to guide liquid from the liquid entry port, along the surface of the skin for the elution of materials on the skin surface, and then to the liquid exit port for recovery;
- wherein the liquid entry port, the liquid exit port and the guide channel are all located at the planar surface such that when the sampling head is held in contact with the skin to form the seal:
  - (i) the guide channel will form a contact with the skin along the surface of the guide channel, and
  - (ii) when the liquid is present in the sampling head, the liquid flowing from the liquid entry port to the liquid exit port along the guide channel will contact the skin along the guide channel.

2. The device according to claim 1, wherein the guide channel has a smooth and/or continuous shape.

3. The device according to claim 2, wherein the guide channel is curved, coiled, swirled or serpentine.

4. A skin surface sampling system comprising:
a liquid source;
a liquid collection vessel, and
a skin surface sampling device as defined in claim 1.

5. The system according to claim 4, wherein positive pressure is used to propel liquid out from the liquid source, through the skin surface sampling device, and back to the liquid collection vessel.

6. The system according to claim 5, wherein a positive displacement pump is fitted to the liquid source.

* * * * *